(12) United States Patent
Hansen et al.

(10) Patent No.: US 11,498,065 B2
(45) Date of Patent: Nov. 15, 2022

(54) POSITIVE DISPENSE VERIFICATION SENSOR

(71) Applicant: BECTON DICKINSON AND COMPANY, Franklin Lakes, NJ (US)

(72) Inventors: Timothy Roy Hansen, Spring Grove, PA (US); Zhou Tong, Ellicott City, MD (US)

(73) Assignee: BECTON DICKINSON AND COMPANY, Franklin Lakes, NJ (US)

( * ) Notice: Subject to any disclaimer, the term of this patent is extended or adjusted under 35 U.S.C. 154(b) by 641 days.

(21) Appl. No.: 16/344,632

(22) PCT Filed: Oct. 26, 2017

(86) PCT No.: PCT/US2017/058567
§ 371 (c)(1),
(2) Date: Apr. 24, 2019

(87) PCT Pub. No.: WO2018/081446
PCT Pub. Date: May 3, 2018

(65) Prior Publication Data
US 2020/0061601 A1 Feb. 27, 2020

Related U.S. Application Data

(60) Provisional application No. 62/414,113, filed on Oct. 28, 2016.

(51) Int. Cl.
*B01L 3/02* (2006.01)
*G01N 35/10* (2006.01)
(Continued)

(52) U.S. Cl.
CPC ............ *B01L 3/0241* (2013.01); *C12M 1/26* (2013.01); *C12M 33/04* (2013.01); *G01N 35/1016* (2013.01); *G01V 8/16* (2013.01)

(58) Field of Classification Search
None
See application file for complete search history.

(56) References Cited

U.S. PATENT DOCUMENTS 6,235,534 B1 * 5/2001 Brookes ............. G01N 35/1016
422/119
7,282,367 B2 * 10/2007 Kawamura ............ G01N 21/51
436/55
(Continued)

FOREIGN PATENT DOCUMENTS

JP H05164765 A 6/1993
JP H0735759 A 2/1995
(Continued)

OTHER PUBLICATIONS

Examination Report issued in corresponding Australian Patent Application No. 2017347830 dated Sep. 28, 2021, 3 pp.
(Continued)

*Primary Examiner* — Brian R Gordon
(74) *Attorney, Agent, or Firm* — Botos Churchill IP Law LLP

(57) ABSTRACT

Systems and methods for positive dispense verification are disclosed. In one embodiment, a system has a plurality of light emitters. The light from the emitters is directed toward a plurality of light detectors across a proximately horizontal plane. The liquid dispense device is positioned above the horizontal plane of light emission from the plurality of light emitters to the plurality of light detectors such that the dispensed liquid will travel through the horizontal plane defined by the emitted light and onto the container being inoculated. Each of the plurality of detectors is coupled to an amplifier. The amplifier generates a signal in response to an interrupt in the transmission of light from the light emitters to the light detectors when the light path is disrupted by the (Continued)

dispense of liquid confirming the liquid was dispensed onto the container.

15 Claims, 3 Drawing Sheets

(51) Int. Cl.
 *C12M 1/26* (2006.01)
 *G01V 8/16* (2006.01)

(56) References Cited

U.S. PATENT DOCUMENTS

| | | | |
|---|---|---|---|
| 7,892,494 B2 * | 2/2011 | Robertson | B01L 3/0241 422/523 |
| 2005/0058387 A1 | 3/2005 | Arnold et al. | |
| 2008/0252679 A1 * | 10/2008 | Pierik | B01J 19/0046 347/19 |
| 2008/0305012 A1 | 12/2008 | Camenisch | |
| 2010/0265287 A1 | 8/2010 | Govyadinov et al. | |

FOREIGN PATENT DOCUMENTS

| | | |
|---|---|---|
| JP | H1073603 A | 3/1998 |
| JP | 2005062168 A | 3/2005 |
| JP | 2005134167 A | 5/2005 |
| JP | 2009520963 A | 5/2009 |
| JP | 2009168816 A | 7/2009 |
| JP | 2016515920 A | 6/2016 |
| WO | 2007071575 A1 | 6/2007 |
| WO | 2014139568 A1 | 9/2014 |

OTHER PUBLICATIONS

Japanese Office Action issued in JP application No. 2019-522929 dated Oct. 7, 2021, 12 pp.
Office Action issued in corresponding Japanese Patent Application No. 2019-522929 dated Jun. 22, 2021, pp. 11.
International Search Report issued in Application No. PCT/US2017/058567 dated Jan. 23, 2018.
Decision to Grant issued in corresponding Japanese Patent Application No. 2019-522929 dated Jun. 21, 2022 (5 pp.).

* cited by examiner

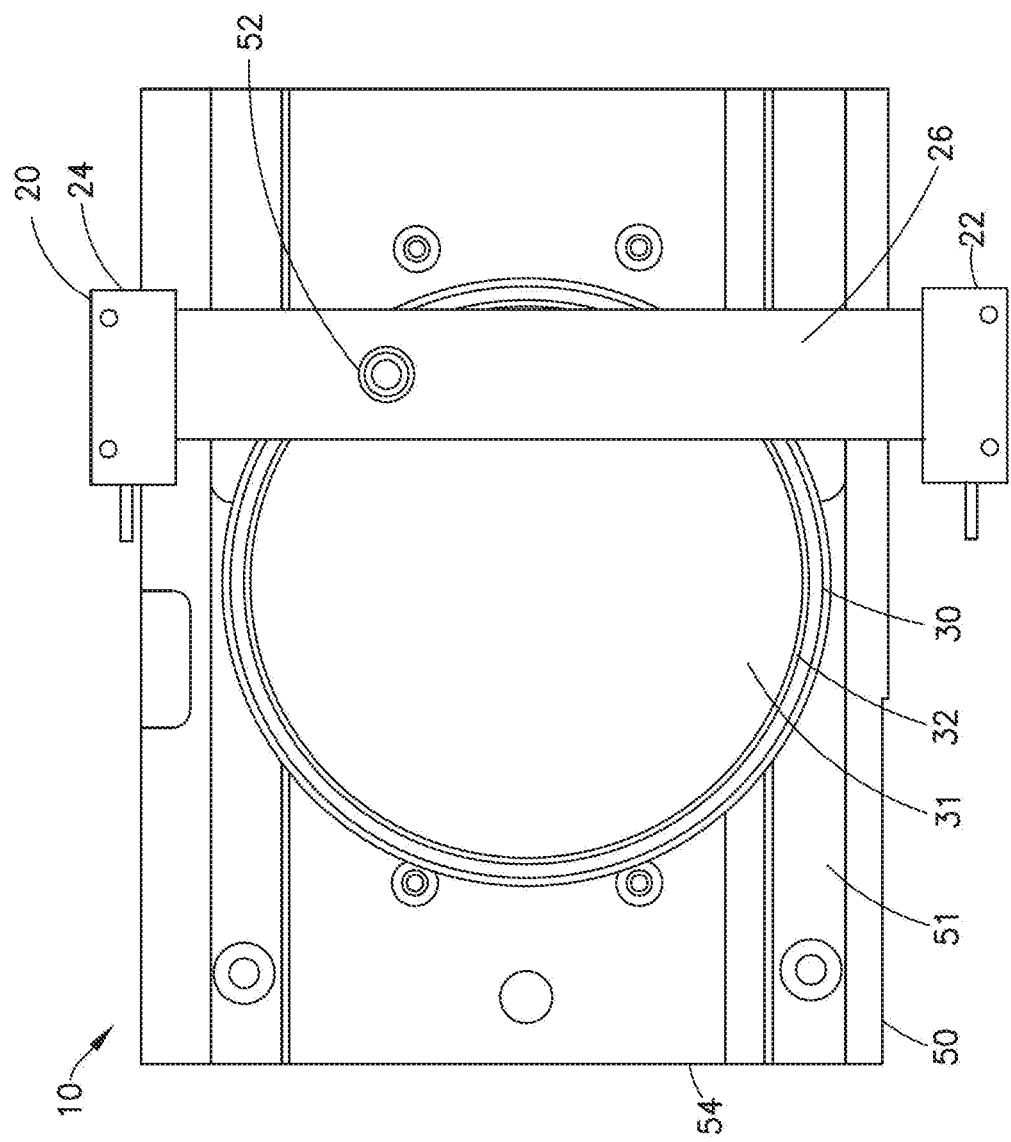

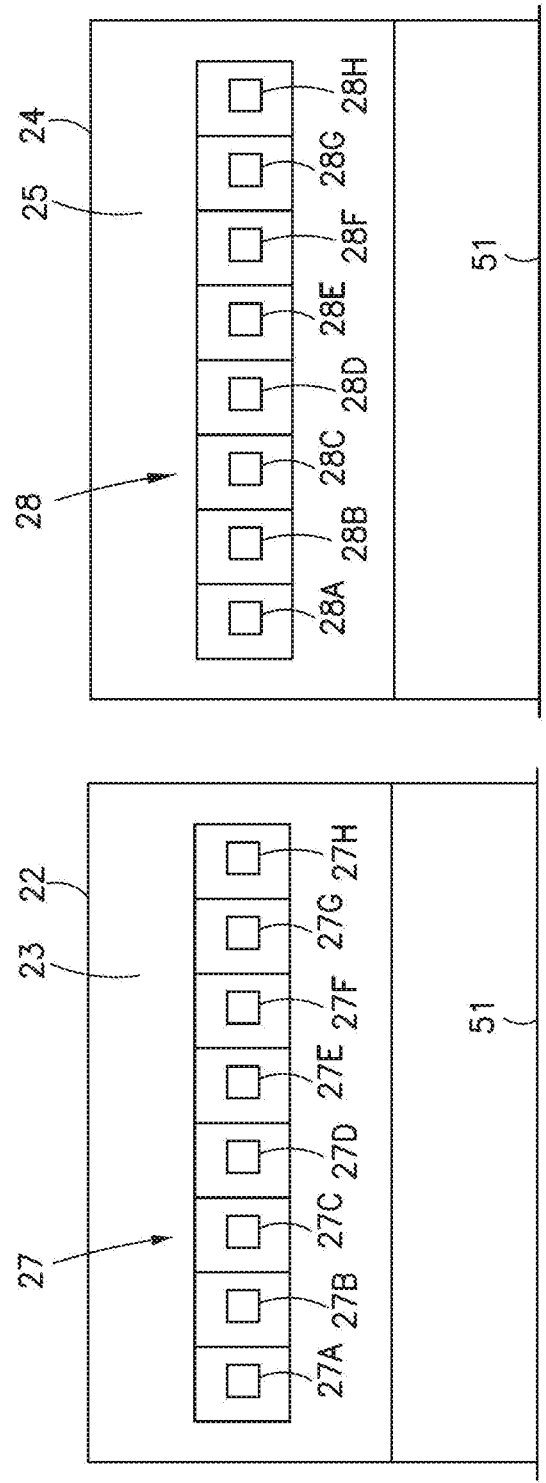

POSITIVE DISPENSE VERIFICATION SENSOR

CROSS-REFERENCE TO RELATED APPLICATIONS

The present application is a national phase entry under 35 U.S.C. § 371 of International Application No. PCT/US2017/058567, filed Oct. 26, 2017, published in English, which claims the benefit of U.S. Provisional Application No. 62/414,113, which was filed on Oct. 28, 2016, all of which are incorporated herein by reference.

TECHNICAL FIELD

The present invention relates to systems and methods for verifying when a dispensing device, such as a pipette, has successfully dispensed a sample into a container or slide.

BACKGROUND

Various systems exist to streamline and increase efficiency for inoculation and testing of samples. To inoculate a sample container, a pipette is often used to dispense the sample into the container. To ensure that a positive dispense or lack thereof is correctly detected, several techniques are known, such as vision systems and pressure monitoring methods. In vision systems, a camera is sometimes used to capture a drop of a sample. To detect a positive dispense accurately, complex image processing and analysis are often required. In pressure monitoring systems, a sensitive pressure transducer is built in a pipetting channel such that it can detect the pressure change during a dispense. However, for pressure systems in particular, no existing pressure transducers are capable of detecting the distinction between a droplet clinging to a tip of a pipette and a droplet that has dispensed from the pipette. Moreover, vision, pressure and other existing techniques are expensive, consume a great deal of physical space, lack reliability or have a combination of these limitations. These challenges become more pronounced as sample (i.e., droplet) sizes become smaller.

Thus, there is a need for improved systems and methods for accurate positive dispense verification of liquids.

BRIEF SUMMARY

Systems and methods for positive dispense verification are disclosed. In one embodiment, a system has a plurality of light emitters. The light from the emitters is directed toward a plurality of light detectors across a proximately horizontal plane. "Proximately horizontal" as used herein refers to orientation of the light curtain relative to a plane defined by a surface onto which a liquid dispense device will dispense liquid. However, the light curtain is not required to be parallel to the surface onto which the liquid will be dispensed. The liquid dispense device is positioned above the horizontal plane of light emission from the plurality of light emitters to the plurality of light detectors such that the dispensed liquid will travel through the horizontal plane defined by the emitted light and onto the container being inoculated. Each of the plurality of detectors is coupled to an amplifier. The amplifier generates a signal in response to an interrupt in the transmission of light from the light emitters to the light detectors when the light path is disrupted by the dispense of liquid confirming the liquid was dispensed onto the container.

One aspect of the present disclosure relates to a system for positive dispense verification, the system comprising: a plurality of light detectors; a plurality of light emitters, wherein light transmitted from the light emitters is directed toward the plurality of light detectors; a liquid dispense device positioned above a light curtain defined by the light directed from the plurality of light emitters toward the plurality of light detectors such that liquid dispensed from the liquid dispense device will travel through the light curtain; and an amplifier communicatively coupled to the plurality of light detectors, wherein the amplifier generates a signal in response to an interrupt in a transmission of light from the plurality of light emitters to the plurality of light detectors.

In some embodiments, the light curtain is proximately horizontal in relation to a surface onto which the liquid dispense device will dispense liquid. In some embodiments, the light curtain is proximately parallel to a surface onto which the liquid dispense device will dispense liquid. In some embodiments, the plurality of light emitters transmit light between 800 nm and 900 nm. In some embodiments, the plurality of light detectors has approximately the same dimensions as the plurality of light emitters. In some embodiments, the plurality of light emitters includes an array of light emitters that are distributed in a row and spaced approximately equidistant from one another. In some embodiments, the plurality of light emitters includes a plurality of arrays of light emitters that are distributed in rows.

In some embodiments, a space between the liquid dispense device and the light curtain is such that a drop of liquid having a volume of at least ten microliters will span the space. In some embodiments, a droplet of three microliters of liquid dispensed from the liquid dispense device causes the amplifier to generate a signal in response to an interrupt in a transmission of light from the plurality of light emitters to the plurality of light detectors. In some embodiments, the light curtain has no gaps that would allow a droplet of three or more microliters of liquid dispensed from the liquid dispense device to pass through the light curtain without causing the amplifier to generate a signal in response to an interrupt in a transmission of light from the plurality of light emitters to the plurality of light detectors.

In some embodiments, a space between the plurality of light emitters and the plurality of light detectors is large enough to accommodate a target plate. In some embodiments, the system further comprises a conveyor configured to position a target plate (a) between (i) the plurality of light emitters and (ii) the plurality of light detectors and (b) below (i) the liquid dispense device and (ii) the light curtain, such that liquid dispensed from the liquid dispense device will travel through the light curtain and fall onto the target plate. In some embodiments, the light curtain is at an orthogonal angle relative to a travel direction of the conveyor. In some embodiments, the light curtain is at a non-orthogonal angle relative to a travel direction of the conveyor.

In some embodiments, the system further comprises a latching circuit communicatively coupled to the amplifier, wherein the latching circuit retains confirmation that an interrupt in a transmission of light from the plurality of light emitters to the plurality of light detectors occurred. In some embodiments, the latching circuit is only on during time intervals beginning prior to a liquid being dispensed from the liquid dispense device and ending after the liquid has been dispensed. In some embodiments, the system further comprises one or more processors configured to: verify a positive dispense by reading data stored in the latching circuit; and deactivate the latching circuit after a positive dispense has been verified.

Another aspect of the present disclosure relates to a method for positive dispense verification, the method comprising: providing a light curtain by transmitting light from a plurality of light emitters toward a plurality of light detectors; positioning a target plate below the light curtain; positioning a liquid dispense device above the target plate and the light curtain; dispensing a liquid from the liquid dispense device onto the target plate, wherein the dispensed liquid travels through the light curtain; and generating a signal in response to an interrupt in a transmission of light from the plurality of light emitters to the plurality of light detectors caused by the travel of the dispensed liquid through the light curtain.

In some embodiments, the target plate is positioned below the light curtain and within a distance between the plurality of light emitters and the plurality of light detectors. In some embodiments, the liquid dispense device is also positioned such that a space between the liquid dispense device and the light curtain is such that a drop of liquid having a volume of at least ten microliters will span the space. In some embodiments, a signal is generated if a droplet of at least three microliters of liquid is dispensed from the liquid dispense device. In some embodiments, the light curtain has no gaps that would allow a droplet of three or more microliters of liquid to be dispensed from the liquid dispense device onto the target plate without interrupting a transmission of at least some light of the light curtain.

In some embodiments, the method further comprises storing data indicating an interrupt in a transmission of light from the plurality of light emitters to the plurality of light detectors occurred when a signal is generated. In some embodiments, the data indicating an interrupt in a transmission of light from the plurality of light emitters to the plurality of light detectors occurred is stored in a latching circuit. In some embodiments, the method further comprises turning on the latching circuit before a liquid is dispensed from the liquid dispense device; and turning off the latching circuit after data indicating an interrupt in a transmission of light from the plurality of light emitters to the plurality of light detectors occurred is stored in the latching circuit. In some embodiments, the method further comprises verifying a positive dispense by reading data stored in the latching circuit.

BRIEF DESCRIPTION OF THE DRAWINGS

FIG. 1 is a top view of a positive dispense verification system according to one embodiment.

FIG. 2B is a partial section view of the positive dispense verification emitter shown in FIG. 2A.

FIG. 2C is a partial section view of the positive dispense verification receiver shown in FIG. 2A.

DETAILED DESCRIPTION

Figure 2A:
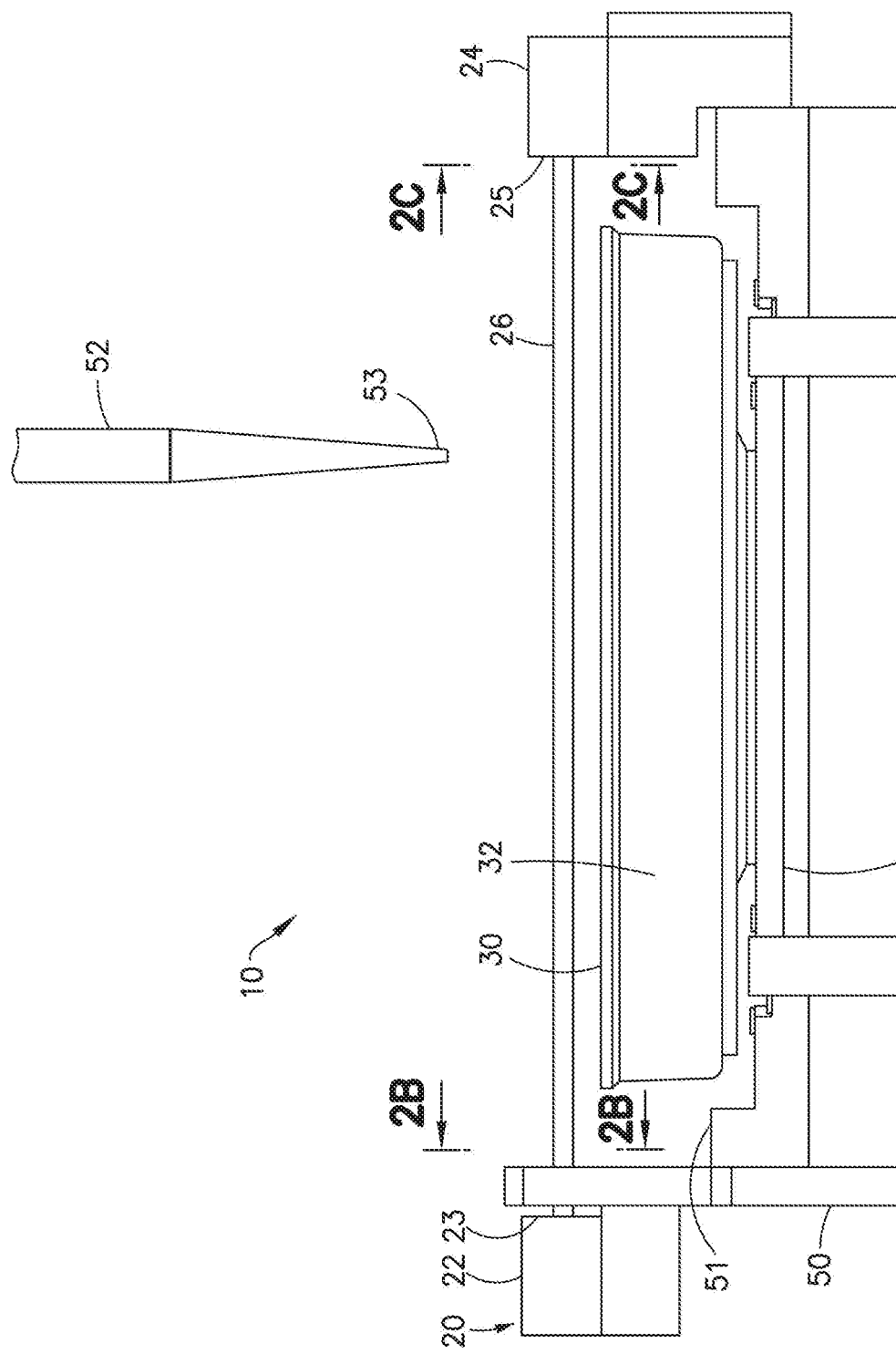
FIG. 2A is a side view of the embodiment shown in FIG. 1.

Embodiments of the present disclosure are described in detail with reference to the drawing figures wherein like reference numerals identify similar or identical elements. It is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

The present invention relates to systems and methods for verifying when a dispensing device, such as a pipette, has successfully dispensed a sample into a container or slide. This is also referred to as positive dispense verification or "PDV." Samples as referred to herein are liquid, but it is contemplated that samples can also be solid. Systems and methods described herein are described in the context of samples used for microbiological testing including procedures for inoculating a growth medium with a sample. However, such description is non-limiting and it is contemplated that the systems and methods described can be used in any context where accurate positive dispense verification of material, e.g., liquid, is desired.

In one aspect, the present invention relates to a system for PDV. FIGS. 1 and 2A illustrate one embodiment of a PDV system 10. System 10 includes a sensor apparatus 20, a target plate 30, and an instrument 50. One exemplary instrument 50 of system 10 is InoqulA™ by Becton Dickinson Kiestra™ ("BD"). When instrument 50 is InoqulA, processes for inoculating, incubating and testing samples are fully automated. InoqulA utilizes three robotic arms for the automated transport of patient sample tubes, pipettes, and any samples disposed therein, to various locations around the instrument. In particular, one robotic arm is configured to transport and dispense samples from a pipette into the target plate. As will be described in greater detail below, it is between the pipette and the target plate that samples are detected by a sensor for PDV.

Returning to the elements of system 10, sensor apparatus 20 is structurally connected to instrument 50 and includes a PDV emitter 22 and a PDV receiver 24. As shown in FIGS. 1 and 2A, PDV emitter 22 is positioned at a distance from PDV receiver 24 so that a physical space exists between the two. In the illustrated embodiment, the space between PDV emitter 22 and PDV receiver 24 comfortably accommodates a plate, such as a plate containing a growth medium. PDV emitter 22 includes a source of light disposed on an inside facing surface 23 of PDV emitter 22 so that when activated, the light is received and detected by an inside facing surface 25 of PDV receiver 24. An elevation of the light source relative to instrument 50 at PDV emitter is approximately the same as an elevation of the light source at PDV receiver 24 so that an axis through each is perpendicular to the direction of gravity. As best shown in FIGS. 1 and 2A, light travelling between PDV emitter 22 and PDV receiver 24 creates a light curtain 26.

PDV receiver 24 includes an amplifier (not shown) configured to process a light signal so that when a momentary interrupt, i.e., a break, occurs in the light received by PDV receiver 24, sensor apparatus 20 captures the momentary change in signal. In one example, a drop of a sample passing through light curtain 26 causes a momentary interrupt in the light, and the interrupt is captured by a latching circuit in one embodiment. The latching circuit of sensor apparatus 20 is configured to latch the signal change (disruption) due to the momentary interrupt. System 10 is further configured so that a computer (not shown) is in electronic communication with sensor apparatus 20 for output to a user of any signal interrupts latched by the latching circuit. The operation of a processor in communication with sensor apparatus 20 is typically asynchronous so that the computer processor can pick up the signal change latched by the sensor at a point in time after it occurs. Elements of system 10 function in a similar manner regardless of whether a polarity of the signal in the interrupted state is positive or negative.

Settings of the amplifier can be adjusted to optimize the necessary volume of a sample drop that can be detected when passing through the light curtain. Put another way, a threshold signal disruption that will be latched by the circuit can be modified through the settings of the amplifier. In one example, the sensor apparatus including PDV emitter and PDV receiver is model BOH00CJ by Balluff and the amplifier is model BAE00NJ by Balluff. When operating per its design specification, the Balluff sensor generates a light curtain 18.5 mm wide and 5 mm in depth.

As shown in FIGS. 1 and 2A, the light source provides light sufficient so that light curtain 26 between PDV emitter 22 and PDV receiver 24 has a width sufficient so that a positive dispense can be detected even when a pipette 52 is positioned at different locations in a direction orthogonal to a length of light curtain 26. For example, if pipette 52 is moved plus or minus five millimeters in such direction, a positive dispense of a sample can still be detected. The device for providing a light source is chosen so that when activated, it produces a light with a wavelength that does not freely transmit through a clear substance such as water. In one example, the wavelength is close to the visible spectrum and is between 800 and 900 nm. In another example, the wavelength is 850 nm. Although applicants do not wish to be held to a particular theory, generating a light curtain with a wavelength between 800 and 900 nm is advantageous because light in this wavelength range is absorbed by water, i.e., transmission of these wavelengths is easily blocked by water, yet light in this range of wavelengths is perceptible relative to ambient lighting. In those embodiments where samples are either aqueous or have optical properties similar to those of water, the wavelength for the light curtain should be tuned to the wavelength described above. If the wavelengths of the light source are not tuned properly, the light forming the curtain may simply be transmitted through the falling sample without disruption, in which case the drop of falling sample will not register. The light sources are selected to have an intensity and a placement such that a sample droplet with a predetermined volume is detectable when light traveling from the PDV emitter 22 is disrupted by the droplet. Other variables that are considered for determining the selected intensity for the light sources include whether or not the sample is a liquid and the ambient lighting conditions.

The device used to generate light is a matter of design choice with the above parameters as guidance. In one example, and as shown in FIG. 2B, the light source can be an array of LEDs 27. LEDs 27A-H are distributed in a row on inside face 23 of PDV emitter 22. There are eight LEDs 27A-H in FIG. 2B, spaced approximately equidistant from one another so that when light is generated, light beams from each LED 27A-H overlap creating light curtain 26 with no gaps that would allow a droplet to pass through the curtain without registering a disrupted signal. The space between LEDs 27A-H is equal to or less than an amount necessary to ensure no such gap exists between adjacent light beams. Eight detectors 28A-H are positioned in a linear array on inside face 25 of PDV receiver 24, as shown in FIG. 2C, so that each detector 28A-H corresponds to an LED 27A-H. It follows that a detector array 28 has approximately the same dimensions as LED array 27 (the combined LEDs 27A-H). In this manner, light is transmitted from each LED 27A-H to each detector in a direction that is approximately orthogonal to the direction in which the plates pass under sensor apparatus 20. Because the direction of light from each LED 27A-H is the same and each light beam at least partially overlaps a light beam from an adjacent LED, a continuous light curtain is produced between PDV emitter 22 and PDV receiver 24, minimizing the possibility that a droplet of sample may fall undetected onto the plate when dispensed from a pipette. Through the inclusion of LEDs and detectors into sensor apparatus 20 in the manner described above, detection of a droplet of partially optically transparent sample (e.g., water), where the volume of the droplet is about three microliter is known to be possible. Indeed, droplets with even smaller volumes are also detectable and adjusting the parameters of the emitter/detector to detect such lower volume droplets is contemplated. This can be accomplished, for example, by adjusting light intensity and a distance between the PDV emitter and the pipette, among other factors described herein. There is no apparent upper limit to the volume of sample that can be detected.

In other examples, LEDs can be distributed over several rows or in other patterns. For any of the above examples, the number of LEDs in an array and/or the number of detectors in an array can be two, three, four, five, six, seven or even more than the eight described above. Generally, the number of LEDs used depends on how precisely the LEDs, the light detectors and the pipette tip can be aligned. For example, if highly precise alignment can be achieved, then two LEDs may be appropriate. However, if precise alignment is difficult to achieve, then more LEDs (e.g. ten LEDs) may be the appropriate number. Although alignment precision may influence the number of LEDs included on the PDV emitter, other factors such as light curtain size may also influence the number of LEDs. Indeed, the number of LEDs on the PDV emitter may be largely a matter of design choice depending on the light curtain parameters. For example, different numbers of LEDs will provide light curtains having different widths (i.e., detection zones). Although the present invention contemplates that the LEDs may be distributed on inside surface 23 of PDV emitter 22 in a variety of patterns that differ from the example described above, the distribution of detectors will mirror any such pattern of LEDs. In other words, any suitable pattern of emitters and detectors will generate a substantially continuous light curtain sufficient to detect droplets passing therethrough when the light source is activated. In still further examples, the number of LEDs can be greater than the number of detectors. However, as a general matter, the number of LEDs will typically be equal to the number of detectors. Although different wavelengths of light might be employed, for light curtains configured to detect drops of liquid that are water or a liquid with optical transmittance similar to water, LEDs that generate infrared light at a wavelength of 850 nm are contemplated as suitable.

System 10 also includes target plate 30. Target plate 30 has a circular base 31 with an annular rim 32 extending distally from circular base 31. An area of circular base 31 and depth of annular rim 32 are sized so that sufficient space exists to inoculate, incubate and test samples. In the illustrated embodiment, target plate 30 is sized to fit within the space between PDV emitter 22 and PDV receiver 24. Target plate 30 includes a bottom surface suited for placement on a conveyor 54 of instrument 50. The bottom surface of target plate 30 is generally flat. In a variant, target plate 30 can be another geometric shape, such as one with a rectangular or polygonal base. In further variants, target plate 30 can be substituted with a broth tube or slides which would then be used to inoculate samples.

Instrument 50 of system 10 is shown in FIGS. 1 and 2A and includes a top surface 51, conveyor 54 and pipette 52. Pipette 52 is connected to a robot arm (not shown) which is part of instrument 50. Of course, a mechanism for securement of pipette 52 to instrument 50 and structure to facilitate movement of pipette 52 are a matter of design choice. For example, and as noted above, instrument 50 can be InoqulA™ by BD, and a robotic arm of InoqulA can retrieve and transport pipette as needed for the inoculation of a plate. In other examples, pipette can be manually transported to an inoculation location to dispense a sample.

FIG. 1 shows how each component of system 10 is positioned relative to the others. Plate 30 is disposed on conveyor 54 of instrument 50. PDV emitter 22 and PDV receiver 24 of sensor apparatus 20 are connected to instrument 50 on opposite sides of conveyor 54. In an operational position as best shown in FIG. 2A, pipette 52 is positioned so that light curtain 26, or a physical space for a light curtain, is disposed in between plate 30 and pipette 52. Sufficient space is maintained between light curtain 26 and pipette 52 at all times so that a drop of the sample on pipette 52 will not be falsely detected. For example, if a drop of a sample is clinging to a tip 53 of pipette 52, a positive response by sensor apparatus 20 will not be indicated. Thus, the LEDs or another light source are positioned on sensor apparatus 20 so that a top limit of light curtain 26 generated by the light source is beneath the lowest point of the largest anticipated sample drop hanging from pipette tip 53 when pipette 52 is at its lowest maneuverable position over light curtain 26. In this manner, there is no circumstance where a sample droplet will contact light curtain 26 without being completely dispensed from pipette 52 prior to passing through light curtain 26. Consequently, the spacing is such that a droplet hanging from the pipette will not be detected unless and until it detaches and falls from the pipette. In some examples, the minimum distance between light curtain 26 and pipette 52 tip is just enough to accommodate a ten microliter drop hanging from pipette 52.

In some embodiments, the system can include two or more sensor apparatus and two or more pipettes dispensing samples into corresponding plates. For example, the system can include two sensor apparatus each having a PDV emitter and receiver with a light curtain therebetween when the PDV emitter is activated. Each sensor apparatus can be positioned at a different location along the conveyor so that two or more plates on the conveyor can advance until one is under each light curtain, at which time a pipette is positioned above each sensor apparatus. In this way, two or more plates can be simultaneously inoculated with PDV.

In other embodiments, the PDV emitter and the PDV receiver can be positioned so that the light curtain decreases or increases in elevation as it travels from the emitter to the receiver. Similarly, the emitter and receiver can be positioned at different locations relative to a length of the conveyor so that the light curtain is at a non-orthogonal angle relative to the length of the conveyor.

In some embodiments, sensor apparatus 20 can be configured so that a trigger indicating a positive dispense can only occur when the pipette is proximal to sensor apparatus 20. Alternatively, sensor apparatus 20 can be configured so that a positive response can only be detected when pipette 52 is dispensed. To configure system 10 in this way, the latching circuit is only turned on to detect a change in signal (i.e., threshold signal disruption) for a narrow window of time from immediately prior to dispensing of pipette 52 until shortly thereafter. In other embodiments, sensor apparatus 20 can be configured to activate only when pipette is dispensed and the target plate is in the correct position on the conveyor for receiving the sample. For example, the latching circuit is turned on for a narrow window of time commencing prior to dispense of pipette 52, and reflective optical sensor(s) (not shown) of system 10 detect whether target plate 30 is under sensor apparatus 20. In this manner, a positive dispense is only detectable when the latching circuit is on and the optical sensor(s) registers a positive detection of target plate 30. It is further contemplated that the sensor apparatus and/or instrument can be configured to recognize a positive dispense in any manner desired for a particular inoculation and testing regime. Sensing techniques can be adapted for use in conjunction with any computer and are not limiting in this regard. For example, latching onto a signal change is not contingent on incorporation of a particular computer into system 10.

Advantages of the system include that it has a high degree of reliability and positive dispense can be verified in a highly accurate manner. For example, when positive dispense is only detected if the pipette and plate are in position, false positives can be greatly reduced, such as those that would occur when a pipette properly dispenses, but misses the target plate below. Similarly, false negatives are mitigated because the sensor has a high degree of sensitivity. The system is also cost effective and can be configured for use in small or unconventional spaces. Another advantage of the system is that it can easily be tailored so that a light curtain generated is wide enough for any expected tolerance range for plates advancing through an instrument. In this manner, if plates do not stop at the same exact location under sensor assembly each time, light curtain will be wide enough so that no false negatives will occur.

In another aspect, the present invention relates to a method for PDV. Throughout the steps of the method, the light source is active and light curtain 26 spans between PDV emitter 22 and PDV receiver 24. In one embodiment, plate 30 ready for inoculation (i.e., supporting a growth medium or agar, not shown), is positioned on conveyor 54 of instrument 50. If not already in position, plate 30 is advanced on conveyor 54 to an inoculation location, such as that shown in FIGS. 1 and 2A. In at least one variant, instrument 50 includes a plate detection light sensor (not shown) at the inoculation location positioned in a manner so that it detects when plate 30 is at a position for inoculation. Of course, other detection mechanisms can also be used to verify the position of plate 30 on instrument 50 such as a weight sensor positioned to detect the weight of plate 30.

At the inoculation location, a common plane passes through plate 30, PDV emitter 22 and PDV receiver 24. In other words, plate 30 is positioned so that at least part of plate 30 lies in between light curtain 26 and conveyor 54 when measured in the direction of gravity.

When pipette is ready to be dispensed, and just prior to dispense of the sample from pipette 52, the latching circuit of sensor apparatus 20 is set. With the latching circuit set, light signals from the PDV emitters 22 are detected by PDV receiver 24 are monitored for any changes. Prior to this time, any changes or other interruptions in the signal received by PDV receiver 24 are not captured by the latching circuit, thus avoiding any false positives. The latching circuit is configured to latch onto any changes in the digital output of the signal generated by the light receiver and in this way operates in a binary manner. In other words, when light travels from PDV emitter to PDV receiver uninterrupted, a first signal based on light received is detected. If the light is interrupted, then a second signal is detected. For example, uninterrupted light results in a detection of "0" while interrupted light results in a detection of "1."

When the sample is dispensed from pipette 52 into plate 30 (i.e. the container being inoculated), a momentary interruption occurs in light curtain 26 spanning between PDV emitter 22 and PDV receiver 24. The light curtain 26 is illustrated as oriented horizontally, but other orientations are possible. The momentary interruption is detected at PDV receiver 24, converted into digital output by the amplifier, and then latched by the latching circuit. Thus, even after the interruption ceases and the signal returns to an uninterrupted state, the latching circuit retains confirmation that a positive dispense occurred. At any time during this process, a command can be entered into a computer integrated with system 10 to query as to whether a positive dispense has occurred. For example, a command can be entered into the computer five seconds after the latching circuit has latched a signal disruption indicative of a positive dispense. The computer will seek out data stored via the latching circuit and output the data for a user. In this case, the computer will identify and then output that a positive dispense has occurred. At this time, the latching circuit is deactivated and the detection window closes as the verification of positive dispense is complete. The method can then be repeated with another sample and plate. As noted above, although the latching circuit is deactivated, light curtain may remain on at all times.

To optimize the method of using system 10 to perform PDV, many external factors can be controlled. For example, ambient light should be controlled to minimize interference with the wavelength of light curtain 26. Dust surrounding instrument 50 and system 10 as a whole should also be controlled and minimized. In addition, if plates are conveyed to sensor apparatus 20 via a conveyor, as described in some examples above, the conveyor should be tuned and otherwise checked so that it operates with minimal vibration. This will prevent any vibrations of the conveyor, passed to plates 30, from causing plate 30 to contact light curtain 26, and therefore avoid false positive detections.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system for positive dispense verification, the system comprising:
   a plurality of light detectors;
   a plurality of light emitters, wherein light transmitted from the light emitters is directed toward the plurality of light detectors;
   a liquid dispense device containing liquid positioned above a light curtain defined by the light directed from the plurality of light emitters toward the plurality of light detectors, and the liquid dispense device is configured to be positioned relative to a surface such that the liquid dispensed from the liquid dispense device travels through the light curtain onto the surface; and
   an amplifier communicatively coupled to the plurality of light detectors, wherein the amplifier generates a signal in response to an interrupt in a transmission of light from the plurality of light emitters to the plurality of light detectors.

2. The system of claim 1, wherein the light curtain is configured to be one of proximately horizontal or proximately parallel in relation to the surface onto which liquid from the liquid dispense device is dispensed.

3. The system of claim 1, wherein the plurality of light emitters transmit light between 800 nm and 900 nm.

4. The system of claim 1, wherein the plurality of light detectors has approximately the same dimensions as the plurality of light emitters.

5. The system of claim 1, wherein the plurality of light emitters includes an array of at least three light emitters that are distributed in a row and spaced approximately equidistant from one another.

6. The system of claim 1, wherein the plurality of light emitters includes a plurality of arrays of light emitters that are distributed in rows.

7. The system of claim 1, wherein a space between the liquid dispense device and the light curtain is such that a drop of the liquid having a volume of at least ten microliters will span the space.

8. The system of claim 1, wherein a droplet of three microliters of the liquid dispensed from the liquid dispense device causes the amplifier to generate a signal in response to an interrupt in a transmission of light from the plurality of light emitters to the plurality of light detectors.

9. The system of claim 1, wherein the light curtain has no gaps that would allow a droplet of three or more microliters of the liquid dispensed from the liquid dispense device to pass through the light curtain without causing the amplifier to generate a signal in response to an interrupt in a transmission of light from the plurality of light emitters to the plurality of light detectors.

10. The system of claim 1, further comprising the surface; wherein the surface is a target plate onto which the liquid is to be dispensed; wherein a span of the space between the plurality of light emitters and the plurality of light detectors is large enough so that the target plate fits within the span.

11. The system of claim 10 further comprising:
   a conveyor configured to position the target plate (a) between (i) the plurality of light emitters and (ii) the plurality of light detectors and (b) below (i) the liquid dispense device and (ii) the light curtain, such that the liquid dispensed from the liquid dispense device will travel through the light curtain and fall onto the target plate supported on the conveyor.

12. The system of claim 11, wherein the light curtain is at an angle relative to a travel direction of the conveyor.

13. The system of claim 1 further comprising:
   a latching circuit communicatively coupled to the amplifier, wherein the latching circuit retains confirmation that an interrupt in a transmission of light from the plurality of light emitters to the plurality of light detectors occurred wherein the latching circuit is only on during time intervals beginning prior to the liquid being dispensed from the liquid dispense device and ending after the liquid has been dispensed.

14. The system of claim 13 further comprising:
   one or more processors configured to:
      verify a positive dispense by reading data stored in the latching circuit; and
      deactivate the latching circuit after a positive dispense has been verified.

15. The system of claim 11, wherein the light curtain is at a non-orthogonal angle relative to a travel direction of the conveyor.

* * * * *